May 9, 1972
F. W. ANDERSON
Plant Pat. 3,165
NECTARINE TREE
Filed Oct. 29, 1970
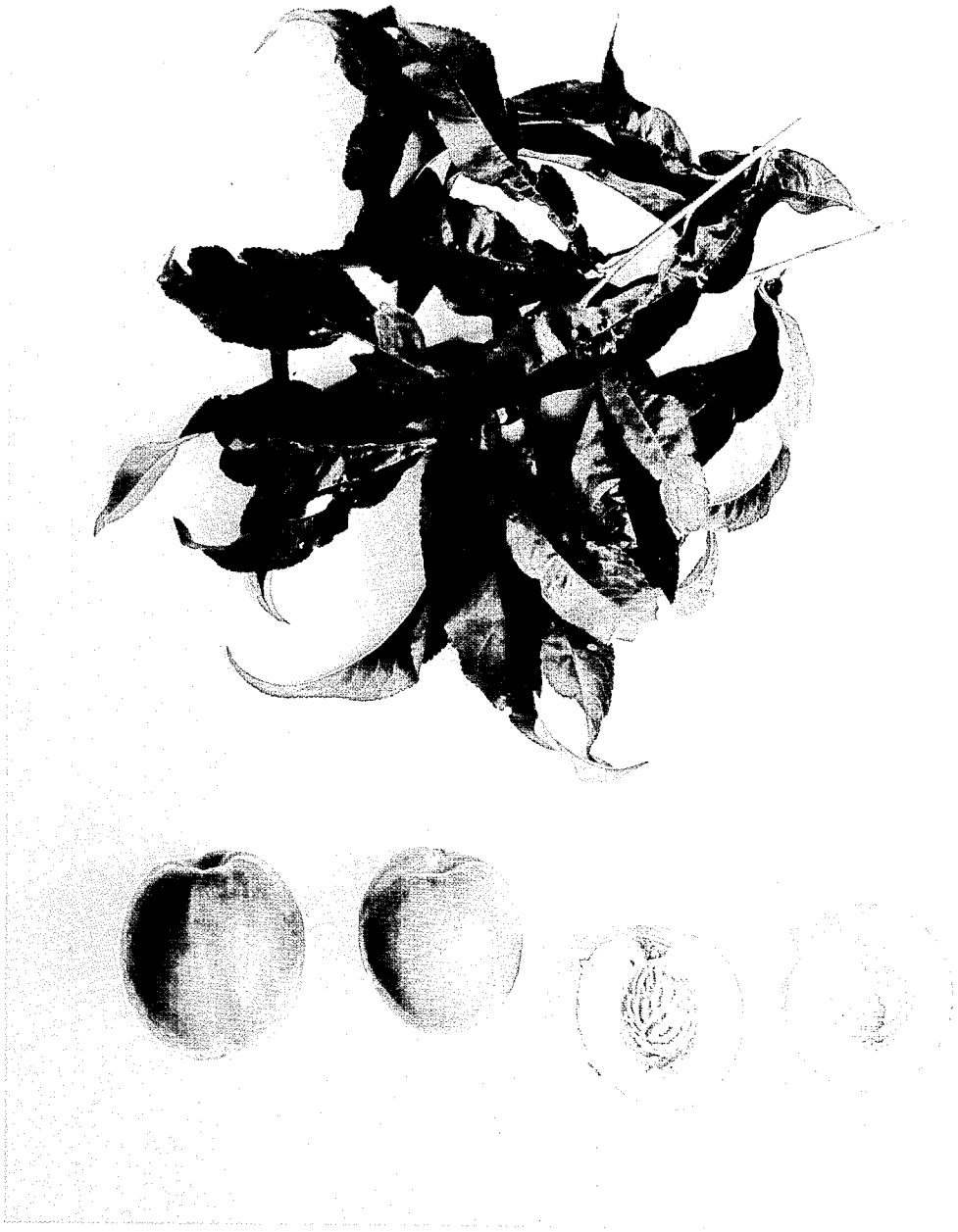
INVENTOR
Frederic W. Anderson
BY
Webster & Webster
ATTORNEYS United States Patent Office Plant Pat. 3,165
Patented May 9, 1972

3,165
NECTARINE TREE

Frederic W. Anderson, Merced, Calif., assignor to Reedley Nursery, Inc., Reedley, Calif.

Filed Oct. 29, 1970, Ser. No. 85,313
Int. Cl. A01h 5/03
U.S. Cl. Plt.—41 1 Claim

ABSTRACT OF THE DISCLOSURE

A variety of nectarine tree which is large, vigorous, spreading, open, and a regular and very productive bearer of medium size, globose to oblong, freestone fruit, of good keeping and shipping quality, which is uniform both as to size and form; the fruit—which is characterized by an unusually long harvest period—having yellow flesh with red at the pit cavity, and skin which is entirely overspread with high red at maturity.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The herein claimed new and distinct variety of nectarine tree was originated by me, in my experimental orchard located as aforesaid, as a selection from a large number of seedlings which resulted from a cross between the Early Sun Grand (U.S. Plant Pat. No. 1,420) and the Red Grand (U.S. Plant Pat. No. 1,060). Such seedlings were maintained by me under careful and continuing observation, and when they bore fruit one such seedling (and which is the present variety) evidenced commercially desirable characteristics. I, therefore, undertook asexual reproduction of such variety preparatory to introducing it to the trade.

ASEXUAL REPRODUCTION OF THE VARIETY

Subsequent to origination and selection by me of the present variety of nectarine tree, in the manner above described, I asexually reproduced it by top-working on mature nectarine trees in my said experimental orchard, and in maturity such reproductions ran true to the original tree in all respects.

SUMMARY OF THE VARIETY

The herein claimed new and distinct variety of nectarine tree is large, vigorous, spreading, open, and a regular and very productive bearer of medium size, globose to oblong, freestone fruit, of good keeping and shipping quality, which is uniform both as to size and form; the fruit—which is characterized by an unusually long harvest period—having yellow flesh with red at the pit cavity, and skin which is entirely overspread with a high red at maturity.

The fruit of the present variety is, more particularly, characterized by the fact that the high red color thereof is attained prior to the Early Sun Grand (U.S. Plant Pat. No. 1,420), the Independence (unpatented), and the Moon Grand (U.S. Plant Pat. No. 2,878).

With respect to the long harvest period of the fruit of the present variety, there is a consequent long market priod—during which the fruit remains firm—spanning, in shelf life, the entire season in the market of the Sun Grand (U.S. Plant Pat. No. 974) and the Star Grand (U.S. Plant Pat. No. 1,646).

BRIEF DESCRIPTION OF THE DRAWING

The drawing is an illustration, by photographic reproduction in color, of twigs with leaves, whole fruit, and one fruit cut into halves with the stone remaining in one-half.

DESCRIPTION OF THE VARIETY

The botanical details of this new and distinct variety of nectarine tree—with color definitions referenced to Maerz and Paul Dictionary of Color—are as follows:

Tree:
- *Size.*—Large.
- *Vigor.*—Vigorous.
- *Growth.*—Spreading.
- *Density.*—Open.
- *Production.*—Very productive.
- *Bearing.*—Regular bearer.

Trunk:
- *Size.*—Medium.
- *Texture.*—Medium.

Branches:
- *Size.*—Medium.

Leaves:
- *Size.*—Large to medium.
- *Form.*—Lanceolate; acutely pointed.
- *Texture.*—Smooth to rugose.
- *Margin.*—Crenate.
- *Petiole.*—Medium length; medium thickness.
- *Glands.*—Number and position—usually 2 on petiole, and often 1 to 4 on blade—medium size; reniform.
- *Color.*—Top side—medium green (23–L–8)—under side—lighter green (22–L–7).

Flowers:
- *Blooming period.*—Medium, as compared with other varieties.
- *Size.*—Large.

Fruit:
- *Maturity when described.*—Hard ripe.
- *Date of first picking.*—June 25, 1970.
- *Date of last picking.*—July 19, 1970.
- *Size.*—Uniform; medium; average diameter axially—2½"—average transversely in suture plane—2⅜".
- *Form.*—Uniform; symmetrical; globose to oblong.
- *Suture.*—Distinct; extends from base to beyond apex; marked depression beyond pistil point.
- *Cavity.*—Elongated in suture plane with suture showing on one side.
- *Apex.*—Short; depressed.

Skin:
- *Thickness.*—Medium.
- *Texture.*—Tough.
- *Tendency to crack.*—None.
- *Down.*—Wanting.
- *Color.*—Bright red (5–L–7).

Flesh:
- *Texture.*—Firm; meaty; melting.
- *Ripens.*—Evenly.
- *Flavor.*—Subacid.
- *Eating quality.*—Good to best.
- *Color.*—Yellow (10–J–6) partially flecked with red (5–K–4). Surface of pit cavity—Red (5–K–5).

Stone:
- *Type.*—Free; parts from flesh smoothly.
- *Size.*—Medium; average length—1¼"—average breadth—1"—average thickness—¾".

*Form.*—Oval.
*Sides.*—Equal.
*Tendency to split.*—Slight.
*Color.*—Brown (14–D–8).

Use: Market, especially those requiring long distance shipping.
Keeping quality: Good.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large, vigorous, spreading, open, and a regular and very productive bearer of medium size, globose to oblong, freestone fruit, of good keeping and shipping quality, which is uniform both as to size and form; the fruit—which is characterized by an unusually long harvest period—having yellow flesh with red at the pit cavity, and skin which is entirely overspread with a high red at maturity; the fruit attaining its high red color prior to the Early Sun Grand, Independence, and Moon Grand, and the relatively long harvest period providing a consequent long market period, during which the fruit remains firm, spanning in shelf life the entire season in the market of the Sun Grand and the Star Grand.

No references cited.

ROBERT E. BAGWILL, Primary Examiner